United States Patent [19]

Armand et al.

[11] Patent Number: 4,542,081
[45] Date of Patent: Sep. 17, 1985

[54] TETRA-ALKYNYL OR -ALUMINATES OF ALKALI METALS, THEIR SOLID SOLUTIONS WITH PLASTIC MATERIALS AND THEIR USE FOR THE CONSTITUTION OF CONDUCTOR ELEMENTS FOR ELECTROCHEMICAL GENERATORS

[75] Inventors: Michel B. Armand, Nancy, France; Fouzia El Kadiri Cherkaoui El Moursli, Sale, Morocco

[73] Assignees: Agence Nationale de Valorisation de la Recherche, Paris; Societe Nationale Elf Aquitaine, Courvevoie, both of France

[21] Appl. No.: 500,191

[22] Filed: Jun. 1, 1983

[30] Foreign Application Priority Data

Jun. 1, 1982 [FR] France ................. 82 09538

[51] Int. Cl.$^4$ ............ H01M 4/62; H01M 6/18
[52] U.S. Cl. ................. 429/192; 429/199; 429/212; 252/62.2
[58] Field of Search ............ 429/192, 191, 50, 212; 252/62.2

[56] References Cited

U.S. PATENT DOCUMENTS

| | | | |
|---|---|---|---|
| 3,020,298 | 2/1962 | Ashby et al. | 260/448 |
| 4,060,674 | 11/1977 | Klemann et al. | 429/194 |
| 4,281,072 | 7/1981 | Wetton et al. | 252/62.2 |
| 4,303,748 | 12/1981 | Armand et al. | 429/192 |

OTHER PUBLICATIONS

Mole et al., Organoaluminum Compounds, 1972, Elsevier Pub. Co. (Melbourne Aus.), pp. 182–184.
Nesmeyanov et al., The Organic Compounds of Boron, Aluminum, Gallium, Indium, and Thallium, 1967, North Holland Pub. Co., pp. 72, 73, 88, 433, and 435.
Gavrilenko et al., Some Reactions of Complex Aluminum Acetylides, Chem. Abst., vol. 67, No. 5, Jul. 31, 1967, p. 2103, 21983w.
Zakharkin et al., Preparation of Complex Aluminum Acetylides of the Type MAlR'4-n-(C:CR)n and their Solvates, Chem. Abs., vol. 63, No. 13, Dec. 20, 1965, 18133a.

Primary Examiner—Donald L. Walton
Attorney, Agent, or Firm—Weiser & Stapler

[57] ABSTRACT

The invention relates to solid solutions constituted by one or several ionic compounds of the formula:

$$(R-C\equiv C)_4 X^-, M^+$$

in which:
X is a trivalent element liable of entering into 4-coordination;
the groups R are aprotic hydrocarbon radicals, that is to say radicals which are non proton donors;
M is an alkali metal;

entirely dissolved within a macromolecular material formed at least in part by a polymer the monomer units of which include at least one hetero-atom, adapted to form bonds of the donor-acceptor type with the cation of the ionic compound.

These solutions can be used for the constitution of solid electrolyte materials of electrochemical generators.

19 Claims, 2 Drawing Figures

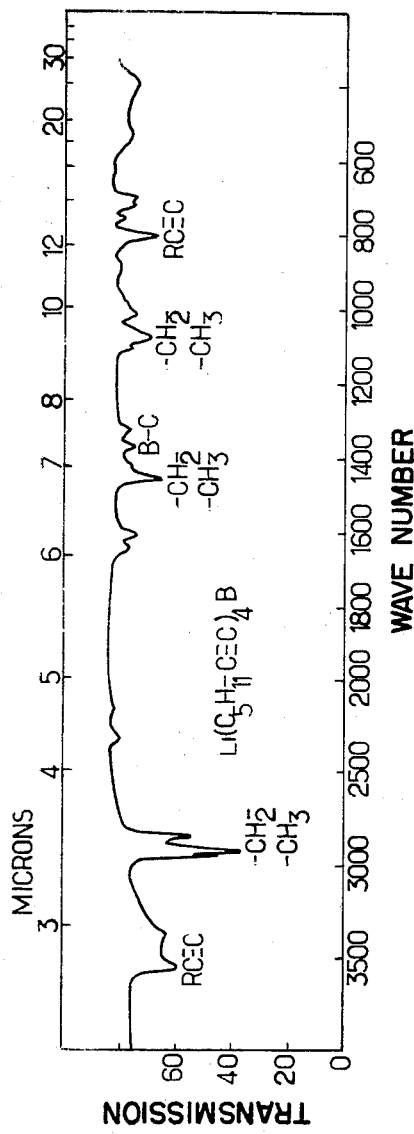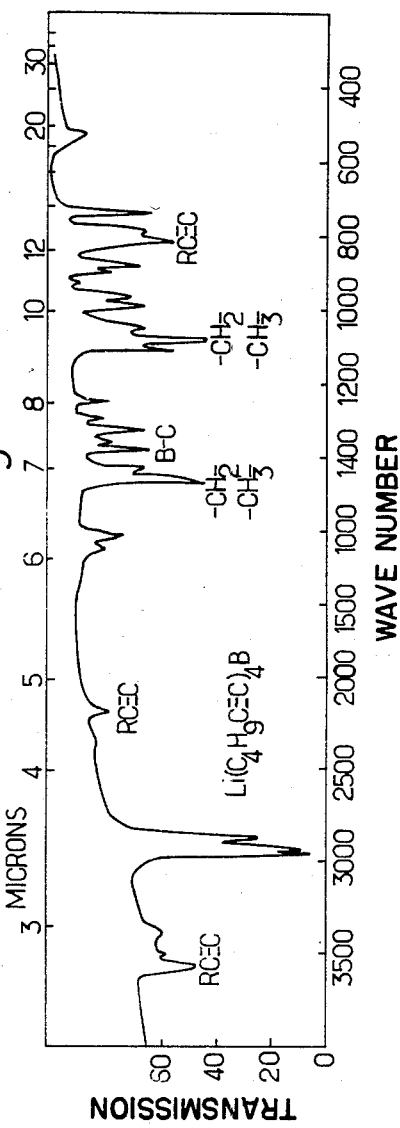

TETRA-ALKYNYL OR -ALUMINATES OF ALKALI METALS, THEIR SOLID SOLUTIONS WITH PLASTIC MATERIALS AND THEIR USE FOR THE CONSTITUTION OF CONDUCTOR ELEMENTS FOR ELECTROCHEMICAL GENERATORS

The invention relates to novel solid solutions substantially constituted by ionic compounds dissolved within a macromolecular material.

The invention relates more particularly to solid solutions essentially constituted by ionic compounds of the formula $M^+X^-$, in which M is a cation derived from a alkali metal or ammonium ion, and $X^-$ is an anion having a behaviour similar to that of a strong acid, which ionic compounds are dissolved within a macromolecular material formed at least in part of one or several homo and/or copolymers derived from one or several monomer units including at least one hetero-atom, particularly oxygen or nitrogen, liable to form bonds of the donor-acceptor type with the cation of the ionic compound.

More particularly, the invention relates to solid solutions substantially constituted by the above said ionic compounds dissolved in at least certain plastic materials, such as those which have been described in European patent application No. 0 013 199 entitled "Electrochemical generators for the production of current and novel materials for their manufacture."

The solid solutions according to the invention are endowed with cationic conductivity, sufficient to be useful for the production of solid electrolyte materials for the constitution of electrochemical generators, preferably rechargeable. These solid solutions are also applicable to the constitution of electrodes of electrochemical generators, when these electrodes are constituted by the product of agglomeration into a composite mass of the active material of the latter and, if necessary, a compound inert to electronic conduction, on the one hand, and the above said solid solution, on the other hand.

It is self-evident that the solid solutions according to the invention may resort to any other type of plastic materials, to the extent that their characteristics of reciprocal solubility are sufficient for the production of a solid solution having a cationic conductivity of $10^{-5} ohms^{-1}.cm^{-1}$, preferably at a temperature not exceeding 130° C.

The invention also relates to novel materials with ionic conduction, particularly caationic, more particularly a novel polymeric solid electrolyte constituted at least in part by a solid solution of one or several of the above-said ionic compounds, entirely dissolved within a macromolecular material formed at least in parts by a polymer, whose monomer units (of one or several types) include at least one heteroatom, particularly oxygen or nitrogen, adapted to form bonds of the donor-acceptor type with the cation of the ionic compound.

FIG. 1 is an IR spectrum of the compound lithium tetraheptynyl borate.

FIG. 2 is an IR spectrum of the compound lithium tetrahexinyl borate.

The ionic compounds entering into the constitution of the solid solutions according to the invention may be represented by the following general formula:

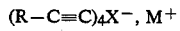

in which:
X is a trivalent element capable of entering into coordinance 4, such as boron or aluminum;
the groups R are aprotic hydrocarbon radicals, that is to say radicals which are non-donors of protons;
M is an alkali metal such as lithium, sodium and potassium.

The hydrocarbon groups R are selected from among those which permit the ionic compounds so formed to form mutual solid solutions with the plastic materials, more particularly with compounds of the polyether type, such as are defined in the above-said European patent application, of again with plastics materials formed of hydrocarbon macromolecules carrying side-chains of the polyether type.

Advantageously, the groups R contain each a number of carbon atoms not exceeding 15. They are also preferably constituted by alkyl or aralkyl groups. They are identical or different from one another, within the same ionic compound.

According to an advantageous modification of the invention, certain of the carbon atoms of these hydrocarbon groups are replaced by heteroatoms such as atoms of oxygen, of sulphur, or of nitrogen.

In the ionic compounds entering into the constitution of preferred solid solutions of the invention, the groups R are constituted by alkyl groups containing from 1 to 8 carbon atoms, for example from 4 to 6, preferably less than 4, carbon atoms or by arylalkyl groups comprising 8 to 15 carbon atoms in which the aryl group is either a phenylene group seperated from the closest of the carbon atoms taking part in the triple bond of the corresponding alkynyl group, by at at least one dimethylene group, preferably trimethylene, or a terminal phenyl group.

It is also possible to represent the formula of the ionic compound entering into the constitution of the solid solutions of the invention in the following manner:

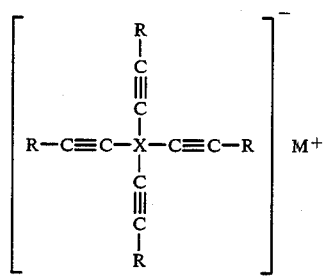

Those of the ionic compounds entering into the constitution of the solid solutions according to the invention and in which X is constituted by boron, are named below "tetraalkynyl borates of alkali metals", and those in which X is aluminum; "tetraalkynyl alanates of alkali metals."

To prepare the ionic compounds entering into the constitution of the solid solutions according to the invention, and in which M is lithium or sodium, there are reacted at the same time an organolithium derivative and a derivative of organo-magnesium chloride in which the organic group is constituted by $R-C\equiv C$ group with a halogen derivative, particularly fluorine, of the trivalent element X. The reaction is carried out within an aprotic solvent, such as tetrahydrofurane and acetonitrile, the mixture being then reacted, with an excess of a potassium salt, such as KSCN within an aqueous solution (the potassium salt being liable to be replaced by a salt of another heavy alkali element, such as a cesium salt), the insoluble product finally obtained being then subjected to an ion exchange reaction, with, as the case may be, a lithium or sodium salt.

For the manufacture of the ionic compounds in which M is potassium or a heavier alkali metal, it will not be necessary to proceed with the above indicated terminal ionic exchange reaction.

In a modification, it is possible to replace in the initial reaction the organolithium derivatives or organomagnesium chlorides by organopotassium derivatives, which then enables the direct production of the ionic compounds according to the invention in which M is potassium. However the organo-potassium derivatives are not generally commercially available.

There is described below, by way of example, the application of this process for the production of lithium tetra-alkynyl borate, it being understood that the specialist will be himself able to adapt the reaction conditions, to obtain the other compounds according to the invention.

FIRST STEP

Preparation of lithium alkynyl or magnesium alkynyl chloride according to the following reaction equations:

$$R-C\equiv CH + CH_3Li \rightarrow R-C\equiv CLi + CH_4 \quad (1)$$

$$R-C\equiv CH + CH_3MgCl \rightarrow R-C\equiv CMgCl + CH_4 \quad (2)$$

Conditions of the two reactions:
 ambient temperature
 time: 1 hour
 solvent: THF In the case of the reaction (1), a coloured indicator: triphenyl methane is used. This compound has an acidity (pKa=30) less than that of the alkyne (pKa=26). The formation of the highly red coloured anion $(C_6H_5)_3-C^-$ appears after complete salification of the acetylene carbon: $(C_6H_5)_3-CH + CH_3Li \rightarrow (C_6H_5)_3-C^- = CH_4$ Some drops of alkyne added to this mixture cause this colour to appear.

In the case of magnesium stoichiometric amounts of each reagent are used (use of assayed commercial solutions: $CH_3MgCl$ 3M).

SECOND STEP

One of the reactions (1') or (2') below are employed.

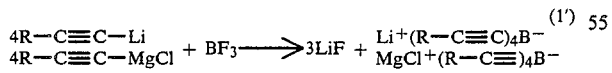
(1')

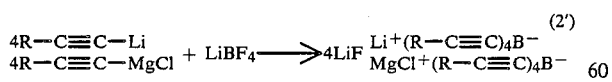
(2')

Conditions of both reactions:
 ambient temperature
 time: 24 H
 solvent: ether for reaction (1') THF for reaction (2')

It is observed that LiF has the same refractive index as the solvents THF and ether. LiF is hence not visible in the organic liquids. The reaction mixture is poured into a large excess of a solution of a potassium salt (KSCN), which results in the reaction:

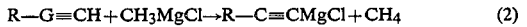

The precipitate collected retains lithium fluoride which is hardly soluble in water (2.7 g/l). The salt is removed in taking up the solid again in acetone which only dissolves $K^+(R-C\equiv C)_4B^-$.

The compound obtained after evaporation is a microcrystalline white powder.

The conversion of the potassium salt into a lithium salt according to the ionic exchange reaction, within an inert solvent, such a acetonitrile (ACN)

$$K^+(R-C\equiv C)_4B^- + LiCl \rightarrow Li^+(R-C\equiv C)_4B^- + KCl$$

The lithium chloride is soluble in THF or ACN, whilst KCl is strictly insoluble, this enables the equilibrium to be completely displaced.

LiCl which is very hydroscopic, must be dehydrated and weighed in an anhydrous atmosphere.

This method enables a standardised solution of the lithium salt (0.2M or 1M) to be obtained, which solution may be used directly for the preparation of the complexes with the poly(ethylene oxide) or poly(propylene oxide), respectively denoted by the abbreviations POE and PPO.

To obtain the corresponding derivatives of aluminium, that is to say the tetraalkynylanates of alkali metals, it is possible to use instead and in place of $BF_3$, compounds of the $LiAlH_4$ or $AlCl_3$ type.

The above-defined ionic compounds have quite satisfactory mutual solution properties with poly(propylene oxide) and even for the compounds in which the R groups are constituted by hydrocarbon chains of short length, with poly(ethylene oxide).

With respect to the macromolecular material entering into the constitution of solid solutions according to the invention, the ratio of the number of hetero-atoms derived from the one or more monomeric units of said polymer to the number of atoms of the alkali metal of said ionic compound is comprised between 4 and 30, particularly 6 and 16. It is self-evident that the proportion of the ionic compound dissolved must be compatible with its solubility level in the selected polymer.

The alkali metal is preferably lithium or sodium.

The preferred plastic materials in which the ionic compounds according to the invention are placed in solution, are homo and/or copolymers derived from monomeric units represented:
either by the following formula:

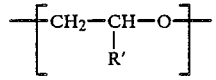

in which R' represents a hydrogen atom or one of the group Ra, $-CH_2-O-Ra$, $-CH_2-O-Re-Ra$, $-CH_2-N=(CH_3)_2$, with Ra representing an alkyl or a cycloalkyl radical including particularly 1 to 16, preferably 1 to 5 carbon atoms, Re representing a polyether radical of the general formula $-(CH_2-CH_2-O)_p-$, p having a value of 1 to 100, particularly from 1 to 2,
or by the following formula:

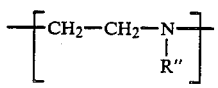

in which R″ represents Ra, —Re—Ra, with Ra and Re having respectively one of the above-indicated meanings,
or by the following formula:

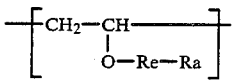

in which Ra and Re have respectively one of the above indicated meanings,
or by the formula:

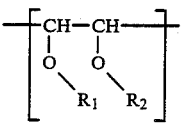

in which $R_1$ and $R_2$ are identical or different and each represent one of the groups Re, Re-Ra with the above meanings, and Re can then represent also a poly-ether of the formula

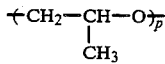

The preparation of the polymeric solid electrolyte may be carried out by the dissolving, in a solvent such as acetonitrile, or again methanol, of the polymer and of the ionic compound, then removal of the solvent, it being understood that a proporation of ionic compound is used less than that for which the solubility threshold is reached.

It is also possible to use any known method not resorting to solvent, for example by dissolving in the molten polymer.

The solid electrolyte produced according to the invention, find particularly advantageous application for the production of both primary and secondary electrochemical generators.

In particular, a solid electrolyte comprising in solution an ionic compound of the above-indicated type, may be associated with a negative electrode, constituted by a material adapted to provide the alkali ion corresponding to the metal of the ionic compound selected and a positive electrode adapted to incorporate the atoms of this metal. It is possible, for example, to provide a negative electrode constituted by the same alkali metal in the form of an alloy, or constituted by an intermetallic compound, an insertion compound or the like. For the positive electrode, it is possible to use any material whose crystalline structure enables the insertion of alkali metals. For example may be mentioned the chalcogenides which permit the diffusion of the alkali metal into their structure. It is possible again, as regard other examples of suitable materials for the formation of the positive electrodes, to refer to the already mentioned European patent application.

It is also possible to produce one of the electrodes, for example the positive one, by forming a composite from the active material of the latter and from these solid solution of the ionic compound, within the same macromolecular material. This composite can also include a compound inert to electronic conduction. It is also possible to resort, to constitute such electrodes and apart from the choice of the cationic compound, to the same methods of constitution as those described in European patent application No. 0013 199.

When these generators are constructed, it is observed that the novel electrolyte according to the invention has the advantage that the anion of the salt or ionic compound in solution is inert with respect to the majority of electrode materials that it is possible to use. This property enables a large number of cycles and stable storage. In addition, this chemical inertness confers on the generators which are thus constructed a very good resistance to thermal shock.

Other characteristics and advantages of the polymeric solid electrolytes according to the invention will appear in the embodiments which follow it being understood that these examples are in no way limiting.

These examples are indicative, particularly of the chemical and/or physical properties of particular ionic compounds of the invention and, in relationship with certain plastic electrolytes constituted with certain of some of them are indicative of the values of temperatures in °C. for which the conductivities are equal to about $10^{-5}\Omega^{-1}cm^{-1}$ (To $-10^{-5}$), even to
$10^{-4}\Omega^{-1}cm^{-1}$ (To $-10^{-4}$).

These measurements have been carried out in vacuum, so as to remove any trace of moisture and/or of solvent.

In all these examples, the macromolecular material is, as the case may be, a poly-(ethylene oxide) (POE) or a poly-(propylene oxide) of molecular weights equal or higher than 900,000. The electrolyte has been obtained by dissolving 1 g of this poly-(ethylene oxide) or this poly-(propylene oxide) in 35 ml of acetonitrile, then the addition of the ionic compound, to obtain atomic ratios O/Li or O/Na which are indicated below.

The solution so obtained is cast on a polytetrafluoroethylene support, to a thickness of 5 mm, then stoved at 60° C. for 3 hours.

The conductivity measurements were done by the techniques described by E. SCHOULER et al, J. Chim. Phys. 9 1309/16 (1973) and D. RAVAINE et al, J. Chim. Phys. 5 (93-70 (1974).

By application of the above-described process there were manufactured, from corresponding raw materials, the following compounds (1) lithium tetraheptynyl borate

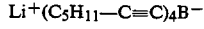

whose IR spectrum is reproduced in FIG. 1 attached; which provides the representative graph of the variations in transmittance as a function either of the wavelength (in microns), or of the number of waves in $cm^{-1}$.

(2) lithium tetrahexinyl borate

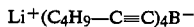

in which the IR spectrum is reproduced in FIG. 2 attached, under the same conditions as with respect to the preceding compound.

(3) potassium tetra(phenyl-pentynyl)borate $$K^+(C_6H_5-(CH_2)_3-C\equiv C)_4B^-$$

(4) lithium tetra(phenyl-pentynyl)borate $$Li^+(C_6H_5-(CH_2)_3-C\equiv C)_4B^-$$

In the table which follows there are provided the electrochemical data which results from the 4 foregoing compounds, after dissolving in POE and PPO, in relative atomic proportions which are seen also from the table.

| Ionic compound | Macromolecular material | O/M* | T$\sigma$ 10$^{-5}$ | T$\sigma$ 10$^{-4}$ |
|---|---|---|---|---|
| (1) | PPO | 8 | 90 | >130 |
| (1) | PPO | 12 | 77 | >130 |
| (2) | POE | 8 | 91 | >130 |
| (2) | POE | 12 | 72.1 | 103.5 |
| (3) | POE | 12 | 54.3 | 104 |
| (4) | POE | 10 | 67.5 | 106 |

*M = lithium, except for the compound (3), case in which M is potassium.

These results testify to the ionic conductivity of the materials so obtaained, which conductivity is sufficient to permit their use in electrochemical generators of the type described.

The lengthening of the alkyl groups (R) is manifested by a reduction in the solubility of the compounds obtained in POE. This solubility in PPO is less affected. It is particularly advantageous to constitute the solid solutions according to the invention with products such as the following:

$$Li^+(CH_3-C\equiv C)_4B^-$$
$$Li^+(C_2H_3-C\equiv C)_4B^-$$
$$Li^+(C_3H_7-C\equiv C)_4B^-$$
$$Li^+(C_2H_5-C\equiv C)_2(CH_3-C\equiv C)_2B^-$$

or the corresponding salts of sodium or potassium.

The introduction of a phenyl (or phenylene) group into the R chains, at a sufficient distance from the alkynyl linkages, is compatible with POE and manifested in addition by a plasticising effect with regard to the solid solutions formed.

In the same way it is possible to prepare the corresponding tetra-alkynyl-aluminates.

We claim:

1. Solid solution constituted by one or several ionic compounds of the formula:

$$(R-C\equiv C)_4X^-, M^+$$

in which:
X is a trivalent element liable of entering into 4-coordination;
the groups R are aprotic hydrocarbon radicals, that is to say radicals which are non proton donors;
M is an alkali metal
entirely dissolved within a macromolecular material formed at least in part by a polymer the monomer units of which include at leaast one hetero-atom, adapted to form bonds of the donor-acceptor type with the cation of the ionic compound.

2. Solid solution according to claim 1, wherein X is selected from among boron or aluminium.

3. Solid solution according to claim 1, wherein M is selected from among lithium, sodium and potassium.

4. Solid solution according to claim 1, wherein the monomer units include at least one hetero-atom selected from among oxygen or nitrogen.

5. Solid solution according to claim 1, wherein in the ionic compound, the groups R each contain a number of carbon atoms not exceeding 15.

6. Solid solution according to claim 1, wherein in the ionic compound, the groups R each contain a number of carbon atoms not exceeding 15 and are constituted by alkyl or aralkyl groups.

7. Solid solution according to claim 1, wherein the R groups are constituted by alkyl groups containing from 1 to 8 carbon atoms.

8. Solid solution according to claim 1, wherein the R groups are constituted by alkyl groups containing from 4 to 6 carbon atoms.

9. Solid solution according to claim 1, wherein the R groups are constituted by alkyl groups containing less than 4 carbon atoms.

10. Solid solution according to claim 1, wherein the R groups are constituted by arylalkyl groups comprising from 8 to 15 carbon atoms in which the aryl group is either a phenylene group separated from the closest of the carbon atom taking part in the triple bond of the corresponding alkinyl group by at least one dimethylene group, or a terminal phenyl group.

11. Solid solution accordind to claim 1, wherein the R groups are constituted by arylalkyl groups comprising from 8 to 15 carbon atoms in which the aryl group is a phenylene group separated from the closest of the carbon atom taking part in the triple bond of the corresponding alkinyl group by at least one trimethylene group.

12. Solid solution according to claim 1, wherein the macromolecular material is constituted by poly(ethylene oxide) or poly(propylene oxide).

13. Solid solution according to claim 1, wherein the ratio of the number of hetero-atoms derived from the monomer units of the above said macromolecular material to the number of atoms of the alkali metal of said ionic compound is comprised between 4 and 30.

14. Solid solution according to claim 1, wherein the ratio of the number of hetero-atoms derived from the monomer units of the aboe said macromolecular material to the number of atoms of the alkali metal of said ionic compound is comprised between 4 and 16.

15. An electrochemical generator for producing electrical current, comprising a negative electrode and a positive electrode separated from each other by means of a solid macromolecular electrolyte material having therein a solid solution according to any one of claims 1, 2, 3, 4, 5, 6, 7, 8, 9, 10, 11, 12, 13 or 14.

16. An electrochemical generator for producing electrical current, comprising a negative electrode and a positive electrode separated from each other by means of a solid macromolecular electrolyte material having therein a solid solution according to claim 1, one of said electrodes comprising said electrolyte material and said solid solution.

17. The electrochemical generator of claim 16 wherein said electrode comprising said electrolyte material and said solid solution is the positive electrode.

18. The electrochemical generator of claim 16 wherein said negative electrode comprises a material adapted to supply a corresponding alkali ion to the ionic compound of said solid solution and said positive electrode is adapted to incorporate the atoms of said metal.

19. An electrode structure in which the electrode material of said structure comprises solid macromolecular electrolyte material having dissolved therein a solid solution of an ionic compound of the formula:

$$(R-C\equiv C)_4 X^-, M^+$$

in which:

X is a trivalent element for entering into 4-coordination;

the groups R being aprotic hydrocarbon radicals which are non proton donors;

M is an alkali metal entirely dissolved with said macromolecular material formed at least in part by a polymer the monomer units of which include at least one heteroatom for forming bonds of the donor-acceptor type with the cation of the ionic compound.

* * * * *